(12) United States Patent
Yang

(10) Patent No.: US 12,263,313 B2
(45) Date of Patent: Apr. 1, 2025

(54) URINARY SYSTEM CATHETER USING ETHANOL EXTRACT OF PROPOLIS AS COATING AND PREPARATION METHOD THEREOF

(71) Applicant: Sichuan University, Chengdu (CN)

(72) Inventor: Luo Yang, Chengdu (CN)

(73) Assignee: Sichuan University, Chengdu (CN)

( * ) Notice: Subject to any disclaimer, the term of this patent is extended or adjusted under 35 U.S.C. 154(b) by 0 days.

(21) Appl. No.: 18/733,907

(22) Filed: Jun. 5, 2024

(65) Prior Publication Data

US 2025/0065076 A1 Feb. 27, 2025

(30) Foreign Application Priority Data

Aug. 25, 2023 (CN) .......................... 202311081697.5

(51) Int. Cl.
| | | |
|---|---|---|
| A61K 35/644 | (2015.01) | |
| A61L 29/08 | (2006.01) | |
| A61L 29/16 | (2006.01) | |
| A61M 25/00 | (2006.01) | |
| B01D 11/02 | (2006.01) | |
| C08L 93/00 | (2006.01) | |
| C09D 193/04 | (2006.01) | |
| A61P 31/04 | (2006.01) | |
| C08L 93/04 | (2006.01) | |

(52) U.S. Cl.
CPC ....... *A61M 25/0017* (2013.01); *A61K 35/644* (2013.01); *A61L 29/08* (2013.01); *A61L 29/16* (2013.01); *B01D 11/02* (2013.01); *B01D 11/0265* (2013.01); *B01D 11/0288* (2013.01); *C08L 93/00* (2013.01); *C09D 193/04* (2013.01); *A61L 2300/30* (2013.01); *A61L 2300/404* (2013.01); *A61P 31/04* (2018.01); *C08L 93/04* (2013.01); *C08L 2666/26* (2013.01)

(58) Field of Classification Search
None
See application file for complete search history.

(56) References Cited

PUBLICATIONS

El-Guendouz (Molecules (2016), vol. 21, No. 9, 1208, 18 pages).*
Wang (CN 1528130 A—English translation), 2004.*
Zhang, Qi-an (CN 106213387—English translation), 2016.*
Zhang, Yang (CN 110721095—English translation), 2020.*
CNIPA, Notification of First Office Action for CN202311081697.5, Sep. 23, 2023.
Sichuan University (Applicant), Reply to Notification of First Office Action for CN202311081697.5, w/ (allowed) replacement claims, Oct. 12, 2023.
CNIPA, Notification to grant patent right for invention in CN202311081697.5, Oct. 20, 2023.

* cited by examiner

*Primary Examiner* — Susan Hoffman
(74) *Attorney, Agent, or Firm* — Hemisphere Law, PLLC; Zhigang Ma

(57) ABSTRACT

A urinary system catheter is covered by an ethanol extract of propolis on a surface of the urinary system catheter. The EEP is used as a coating material of the urinary system catheter to prepare an antimicrobial urinary system catheter. The EEP serving as a surface coating can enhance surface hydrophilicity of the urinary system catheter, and clinical operation of the urinary system catheter is facilitated. Meanwhile, the EEP serving as the surface coating can prevent a bacterial biofilm from being formed on the surface of the urinary system catheter, thereby possessing antimicrobial and anti-infective effects, and a high anti-scab capacity. In addition, propolis is a natural substance, has the advantages of good biocompatibility and low cost, and is suitable for mass production. The urinary system catheter prepared by using the EEP as the coating has a good application prospect.

10 Claims, 5 Drawing Sheets

URINARY SYSTEM CATHETER USING ETHANOL EXTRACT OF PROPOLIS AS COATING AND PREPARATION METHOD THEREOF

CROSS-REFERENCE TO RELATED APPLICATION

This application claims priority to a Chinese patent application No.202311081697.5, filed to China National Intellectual Property Administration (CNIPA) on Aug. 25, 2023, which is herein incorporated by reference in its entirety.

TECHNICAL FIELD

The present disclosure relates to the technical field of biomedical materials, particularly to a urinary system catheter using an ethanol extract of propolis (EEP) as a coating and a preparation method thereof.

BACKGROUND

A urinary system catheter refers to a catheter used in a urinary system, and mainly includes a ureteral stent, a catheter, a prostate stent, a cystostomy catheter, a nephrostomy catheter, a percutaneous drainage catheter, an abdominal drainage catheter, a urological guidewire, a urological catheter, a penile implant, etc. The ureteral stent is a specially designed double-ended curled hollow tubular device that is surgically placed inside a patient's ureter. And then, the ureteral stent drains urine to a bladder by expanding the blocked or narrow ureter, thereby reducing the occurrence of fistula in a kidney or the ureter, ensuring an anastomosis between the ureteral stent and the patient's ureter, and promoting wound healing of the patient's ureter. A basic structure of the catheter is a flexible tube that is inserted into the bladder passing through a urethra. Moreover, the catheter is usually made of - latex or silica gel, and is mainly used for solving the problems of uroschesis, difficulty in urination, urinary drainage after surgery, bladder irrigation, etc. At present, the ureteral stent and the catheter are widely used in urinary surgery, and have become indispensable tools for urological surgery and adjuvant therapy.

Although the urinary system catheter, such as the ureteral stent and the catheter, provides a great deal of convenience to the patient, it has been found through long-term clinical applications that some complications are often brought when the ureteral stent or the catheter is left in the patient for a long time. For example, urinary tract infection (UTI), hematuria, stone formation on the wall and lumen of the catheter, bladder stimulation, etc. bring different degrees of pain to the patient and affect the patient's life and work during carrying the catheter. In view of the various complications, the UTI is most common. For patients that need to carry the ureteral stent or the catheter for a short time, they can be administrated by sufficient broad-spectrum antibiotics to treat with the UTI. However, if the urinary system catheter such as the ureteral stent or the catheter is left in the patient for a long time, a surface of the urinary system catheter can generate a scab. Therefore, the treatment for the UTI in view of the patient that need to carry the urinary system catheter for a long time is troublesome, which often needs to pull out the ureteral stent or the catheter to prevent from infection or scab, so that the patient that need to carry the urinary system catheter for a long time must replace with a new ureteral stent or the catheter as soon as possible. Even in this way, residual bacterial microorganisms in the urinary system will again adhere to a new ureteral stent or a new catheter, and a new infection will occur again. Finally, even if a large dose of the broad-spectrum antibiotics is used for the treatment, the effect is not good, and great pain and economic burden are brought to the patient. Therefore, under the current environment where bacteria are highly resistant to drugs, how to effectively prevent the formation of bacterial biofilm on the urinary system catheter is the most important task at present.

At present, researchers are trying to study new biological materials and coatings to inhibit the formation of bacterial biofilm, such as some studies have made coatings by using heparin, diamond, Teflon, silver ions, antimicrobial peptides, etc., used in the urinary system catheter and there are patents that use drug combinations as coatings used in the urinary system catheter (such as Chinese patent application No. CN201811286764.6). However, the application effects of these coatings are very limited, and there are some problems that hinder the clinical application of the coatings. For example, whether the heparin and diamond coatings on the ureteral stents can reduce the formation of bacterial biofilm and can be placed in the patient's body for a long time without forming the scab needs further verification. Although it is found that when the Teflon-coated ureteral stent is placed in the ureter of an experimental pig, the inflammatory hyperplasia of ureteral epithelial cells in the experimental pig body can be reduced, thereby reducing the risk of ureter stenosis; it has not been illustrated whether the coated ureteral stent can be placed in the body for a long time, and whether infection caused by pathogenic bacteria in the urinary system can be reduced. In addition, the effect of silver ion coatings on the urinary system catheter in anti-infection is uncertain; and it is more difficult to mass-produce antimicrobial urinary system catheters using peptides as coatings. There are still few truly applied clinical solutions and materials.

Urinary system catheter-related infections have always been a global problem. Most of the existing anti-infection coating products on the market are developed abroad, and there are fewer independent research and development at home. At the same time, the existing products on the market have poor antibacterial properties and coating obtainability, the costs are all high, and the effects are limited. The industry has been striving to develop a urinary system catheter with high antibacterial capability and low cost.

SUMMARY

In order to solve the problems existing in the related art, the present disclosure provides a urinary system catheter using an ethanol extract of propolis (EEP) as a coating and a preparation method thereof.

The present disclosure provides an antimicrobial and anti-infective urinary system catheter, including a coating of a propolis alcohol extract covered on a surface of the antimicrobial and anti-infective urinary system catheter.

The propolis alcohol extract is the EEP.

A preparation method of the EEP includes the following steps: adding ethanol into propolis to perform ultrasonic extraction to obtain an extract, and filtering the extract to obtain supernatant, thereby obtaining the EEP.

The propolis is propolis powder.

The ethanol is an ethanol solution with a volume percentage in a range of 70% to 90%.

A mass of the ethanol is 25 times to 30 times of a mass of the propolis.

A temperature of the ultrasonic extraction is in a range of 20 degrees Celsius (° C.) to 60° C.; a frequency of the ultrasonic extraction is in a range of 20 kilohertz (kHz) to 40 kHz; a power of the ultrasonic extraction is in a range of 100 watts (W) to 300 W; and a time for the ultrasonic extraction is in a range of 40 minutes (min) to 60 min.

The ethanol is the ethanol solution with the volume percentage of 75%.

The mass of the ethanol is 25 times of the mass of the propolis.

The temperature of the ultrasonic extraction is 60° C., the frequency of the ultrasonic extraction is 37 kHz, the power of the ultrasonic extraction is 100 W, and the time for the ultrasonic extraction is 60 min.

A method for covering the surface of the antimicrobial and anti-infective urinary system catheter with the coating of the propolis alcohol extract is as follows: immersing a urinary system catheter into a solution of the EEP, and then taking out and drying to obtain the antimicrobial and anti-infective urinary system catheter, where a solvent of the solution of the EEP is the ethanol solution with the volume percentage in the range of 70% to 90%.

Further, the urinary system catheter is a ureteral stent, a catheter, a urethral stent, a prostate stent, a cystostomy catheter, a nephrostomy catheter, a percutaneous drainage catheter, an abdominal drainage catheter, a urological guidewire, a urological catheter, or a penile implant.

The present disclosure further provides a preparation method of the antimicrobial and anti-infective urinary system catheter, which includes the following steps: immersing the urinary system catheter into the solution of the EEP, and then taking out and drying to obtain the antimicrobial and anti-infective urinary system catheter, where the solvent of the solution of the EEP is the ethanol solution with the volume percentage in the range of 70% to 90%.

Further, the solvent of the solution of the EEP is the ethanol solution with the volume percentage of 75%; a concentration of the solution of the EEP is in a range of 30 milligrams per milliliter (mg/mL) to 130 mg/mL; a temperature of the immersing is in a range of 30° C. to 40° C.; a time for the immersing is in a range of 6 hours (h) to 24 h; and a temperature for the drying is in a range of 30° C. to 40° C.

Further, the concentration of the solution of the EEP is in the range of 32 mg/mL to 128 mg/mL; the temperature of the immersing is 37° C.; the time for the immersing is 24 h; and the temperature for the drying is 37° C.

Due to that the propolis is antimicrobial, the use of propolis or propolis alcohol extract as a coating has been studied by researchers. For example, U.S. Patent Publication No. US2007003591A1 discloses the use of an EEP (obtained by extracting the propolis using an ethanol solution with a volume percentage of 70%) as a coating for a cardiovascular stent. However, apart from the antimicrobial purpose, a purpose of using the propolis or the propolis alcohol extract as a coating in the above disclosure is completely different from the present disclosure. In that disclosure, a material made of the cardiovascular stent is a biodegradable metal alloy that gradually degrades after implantation, and since the propolis is hydrophobic, the propolis or the propolis alcohol extract is used as a hydrophobic coating to inhibit or delay the degradation process of the metal alloy. This is entirely different from the use of the propolis alcohol extract in the present disclosure, i.e., improving the hydrophilicity of urinary system catheter. Moreover, the propolis alcohol extract in that disclosure does not involve the functions of resisting calcium salt deposition or anti-encrustation.

At present, there is no research or product on using the propolis alcohol extract to prevent catheter-associated UTI. The present disclosure adopts the propolis alcohol extract as the coating to be covered on the surface of urinary system catheter (i.e., the ureteral stent and the catheter, etc.), thereby forming an impermeable film on the surface of the urinary system catheter to reduce surface bacterial biofilm colonization and reducing the occurrence of UTI while carrying the urinary system catheter. Meanwhile, after the propolis alcohol extract is applied to the urinary system catheter as the coating, the calcium salt deposition on the surface of the urinary system catheter can be reduced, and the anti-encrustation is achieved.

In addition, unlike the related art, the present disclosure finds that after the propolis alcohol extract is used as the coating to modify the urinary system catheter, the hydrophilicity of the urinary system catheter is improved, thereby improving the hydrophilicity of the material used in the surgery. Therefore, the material used in the surgery is smooth to be placed, facilitating the surgical operation and the smooth insertion of the urinary system catheter, especially for the situation that the urethra and the ureter have certain damage, stenosis, etc., thereby reducing the resistance caused by friction to facilitate clinical operation.

Therefore, compared with the related art, the present disclosure has the following beneficial effects.

In the present disclosure, the propolis alcohol extract is used as the coating covered on the urinary system catheter to prepare the antimicrobial and anti-infective urinary system catheter. As the surface coating, the propolis alcohol extract can enhance the hydrophilicity of the surface of the urinary system catheter, avoid the problem of discomfort of the patient caused by the friction during the clinical operation, and facilitate the clinical operation of the urinary system catheter. Meanwhile, the propolis alcohol extract as the surface coating prevents the surface of the urinary system catheter from forming a bacterial biofilm, has excellent antimicrobial and anti-infective properties, and performs well in anti-encrustation. In addition, the propolis is a natural substance, which has the advantages of good biocompatibility and low cost, and is suitable for mass production. The urinary system catheter prepared by using the propolis alcohol extract as the coating can effectively solve the problems of the urinary system catheter in the related art (i.e., the clinical operation is inconvenient, the bacterial biofilm is formed, the scab is generated, the biocompatibility is poor, the cost is high, the mass production is difficult, etc.), and has a good application prospect. Moreover, flavonoids and phenolic acids generated by the propolis and the propolis alcohol extract endow the urinary system catheter antimicrobial and anti-calculi properties.

DETAILED DESCRIPTION OF EMBODIMENTS

Figure 1A:
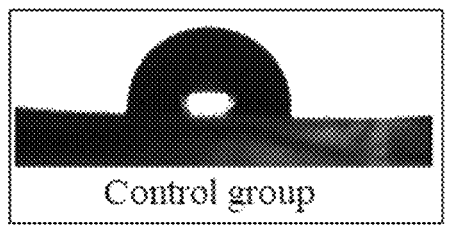
FIGS. 1A-1D illustrate schematic diagrams of measurement results of contact angles between water and surfaces of catheters using EEP with different concentrations as coatings.
Figure 1B:
Figure 1C:
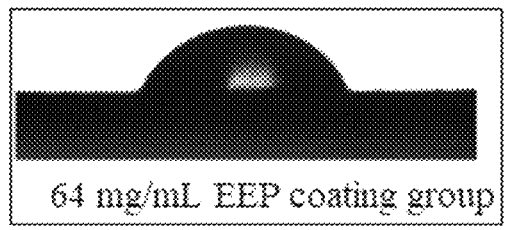
Figure 1D:

Raw materials and devices used in the embodiments of the present disclosure are all known products and are obtained by purchasing commercially available products.

Embodiment 1

The disclosure provides a method for preparing a urinary system catheter (i.e., a ureteral stent, a catheter, etc.) using an EEP as a coating.

Propolis, as described in Pharmacopoeia of the People's Republic of China 2020, is a viscous solid substance formed from plant resin collected by a worker bee of *Apis mellifera* L. species, mixed with secretions from their mandibular and wax glands. The propolis becomes hard and brittle at 20° C. or below. The propolis used in the present embodiment is crude propolis without any processing.

After the EEP is obtained by ultrasonic extraction, a physical impregnation and drying method is used to immerse a ureteral stent and a catheter in the EEP for coating and drying, and then the ureteral stent and the catheter using the EEP as the coating are constructed.

(1) The EEP is prepared by the following steps: cutting the propolis into small pieces, then putting the small pieces of the propolis into a grinder to grind into fine powder, adding an ethanol solution with a volume percentage of 75% into the fine powder of the propolis according to 25 times of a volume of the fine powder of the propolis to perform ultrasonic extraction for 60 minutes (min) to obtain an extract. Specially, a temperature of the ultrasonic extraction is 60 degrees Celsius (° C.); a frequency of the ultrasonic extraction is 37 kilohertz (kHz); and a power of the ultrasonic extraction is 100 watts (W). Thereafter, the extract is stood for 12 hours (h) at room temperature to obtain supernatant, then the supernatant is performed by rotary evaporation and concentration (with a temperature of 40° C.) to obtain a propolis alcohol extract (preserved at −20° C. for a long time). 12.8 grams (g) of the propolis alcohol extract is dissolved in 100 milliliters (mL) of the ethanol solution with the volume percentage of 75% to obtain a mixture, and then the mixture is filtered through a filter membrane with a size of 0.22 micrometers (um) accompanied with sterilization to obtain the EEP with a concentration of 128 milligrams per milliliter (mg/mL).

Two significant ingredients, i.e., total flavonoids content and total phenolic acid content in the prepared EEP are determined by ultraviolet spectrophotometry, and the results are as follows: there exist 274.4±4.4 milligrams per gram (mg/g) of the total flavonoids and 143.7±0.3 mg/g of the total phenolic acid, respectively.

(2) A method for preparing a ureteral stent/catheter modified by using the EEP as the coating includes the following steps. Specially, the ureteral stent and the catheter are commercially available products, which have hydrophobic surfaces and no other drug coatings; the ureteral stent is made from polyurethane; and the catheter is made from latex. The ureteral stent and the catheter are segmented to obtain segmented ureteral stents and segmented catheters; and the segmented ureteral stents and the segmented catheters are immersed in anhydrous ethanol for 30 min for sterilization. Afterwards, the sterilized ureteral stent and the sterilized catheter are immersed in the EEP with three different concentrations respectively (i.e., 32 mg/mL, 64 mg/mL, 128 mg/mL diluted by using the ethanol solution with the volume percentage of 75%), and then are placed in a 37° C. oven for 24 h, thereafter taking out to dry in the 37° C. oven to obtain the ureteral stent and the catheter modified by using the EEP as the coating.

Embodiment 2

The disclosure provides a method for preparing a urinary system catheter using an EEP as a coating.

In addition to preparing the EEP according to the method described in the embodiment 1, the EEP can also be prepared by the following method.

In a first aspect, the method in the present embodiment is performed according to the method described in the embodiment 1, but the temperature of the ultrasonic extraction is 20° C.; the frequency of the ultrasonic extraction is 20 KHz; and the power of the ultrasonic extraction is 300 W.

In a second aspect, the method in the present embodiment is performed according to the method described in the embodiment 1, but a solvent for the extraction of the propolis is changed from the ethanol solution with the volume percentage of 75% to anhydrous methanol.

In a third aspect, the method in the present embodiment adopts impregnation extraction. Specially, the crude propolis is placed in a −20° C. refrigerator overnight and crushed in a mortar to obtain powder of the propolis, and then the powder of the propolis removes wax at a 70° C water bath to obtain wax-removed powder of the propolis. Then, the wax-removed powder of the propolis is weighted and added into the ethanol solution with the volume percentage of 75% according to a solid-liquid ratio of the wax-removed powder of the propolis to the ethanol solution being 1 g: 25 mL, and the ethanol solution added with the wax-removed powder of the propolis is immersed for 1-2 weeks after sealing to obtain supernatant. Thereafter, the supernatant is filter to remove sediment. The EEP solution with a certain concentration is prepared by using an original weight of the crude propolis to deduct the weight of the propolis after removing the sediment.

Beneficial effects of the present disclosure are proved by the following experimental examples.

Experimental Example 1

The present experimental example provides a performance study on the urinary system catheter prepared by using the EEP as the coating according the present disclosure.

(1) Preparation of the urinary system catheter with the coating includes: dividing the ureteral stent and the catheter in to segments with a size of 1 centimeter (cm) as described in the above embodiment 1. The segments are immersed into absolute ethyl alcohol for 30 min for the sterilization. An experimental group takes 2 mL of the EEP with concentrations of 32 mg/mL, 64 mg/mL, and 128 mg/mL in a 12-well plate, and the segments of the ureteral stent and the catheter are immersed at 37° C. in each concentration of the EEP for coating. After 24 h, the segments are taken out and dried in a 37° C. oven. A control group immerses the segments of the ureteral stent and the catheter into the ethanol solution with the volume percentage of 75%, operation method of which is the same as the experimental group. Specially, the EEP with different concentrations is obtained by diluting the EEP prepared in the embodiment 1 with the 75% ethanol solution as a diluent.

(2) Measurement of EEP coating content includes: immersing the segments prepared by using the EEP with different concentrations (i.e., 32 mg/mL, 64 mg/mL, and 128 mg/mL) as the coatings in 10 mL of the ethanol solution with the volume percentage of 75% respectively, and then shaking to fully dissolve the EEP coatings. Thereafter, 0.2 mL of each EEP coating is taken to measure the total flavonoids content and the total phenolic acid content (three parallel samples). The total flavonoids content and the total phenolic acid content are measured by using a chemical chromogenic method with ultraviolet spectrophotometer. The total flavonoids content is compared with standard rutin, and the total phenolic acid content is compared with standard gallic acid. Then, the average surface propolis content is calculated according to the following formula:

$$\frac{\text{total flavonoids content in solution}/274.4 + \text{total phenolic acid content in solution}/143.7}{2 \times \text{surface area of segment}}$$

The results are shown in the following Table 1, indicating that the surfaces of the segments coated with different concentrations of EEP have a certain amount of the EEP, namely that the present disclosure successfully prepares the urinary system catheter modified by using the EEP as the coating.

TABLE 1

Measurement results of propolis concentration on the surfaces of the ureteral stent and the catheter using the EEP as the coating (average value, milligrams per square centimeter abbreviated as mg/cm$^2$)

| EEP coating concentration (mg/mL) | 32 | 64 | 128 |
|---|---|---|---|
| Ureteral stent | 0.721 | 1.598 | 4.072 |
| Catheter | 1.163 | 4.134 | 6.451 |

(3) The contact angle of each group, i.e., between water and the surface of the catheter using the EEP as the coating is measured by using a contact angle goniometer, which is shown in FIGS. 1A-1D; and the measurement results are shown in the following Table 2. The measurement results show that the control group, namely the solvent coating group, has a hydrophobic surface (contact angle greater than 90°) on the catheter, while after being coated with the EEP, its surface changes from hydrophobic to hydrophilic (contact angle less than 90°).

As the concentration of EEP continues to increase, the contact angle decreases. The highest concentration of EEP coating group has a contact angle less than 60°, indicating that the EEP coating improves the hydrophilicity of the surface of the catheter. The surfaces of both the ureteral stent and the catheter are hydrophobic, and the EEP coating can also improve the hydrophilicity of the surface of the ureteral stent. The improvement in the hydrophilicity can avoid discomfort caused by friction during clinical operations, which is beneficial for the smooth use of the catheter and the ureteral stent.

TABLE 2

Measurement results (average value) of the contact angles between the surfaces of the catheters using the EEP with different concentrations as the coatings and water

| EEP coating concentration (mg/mL) | Contact angle with water/° |
|---|---|
| 0 (control group) | 101.90 |
| 32 | 86.87 |
| 64 | 70.82 |
| 128 | 59.33 |

Figure 2:
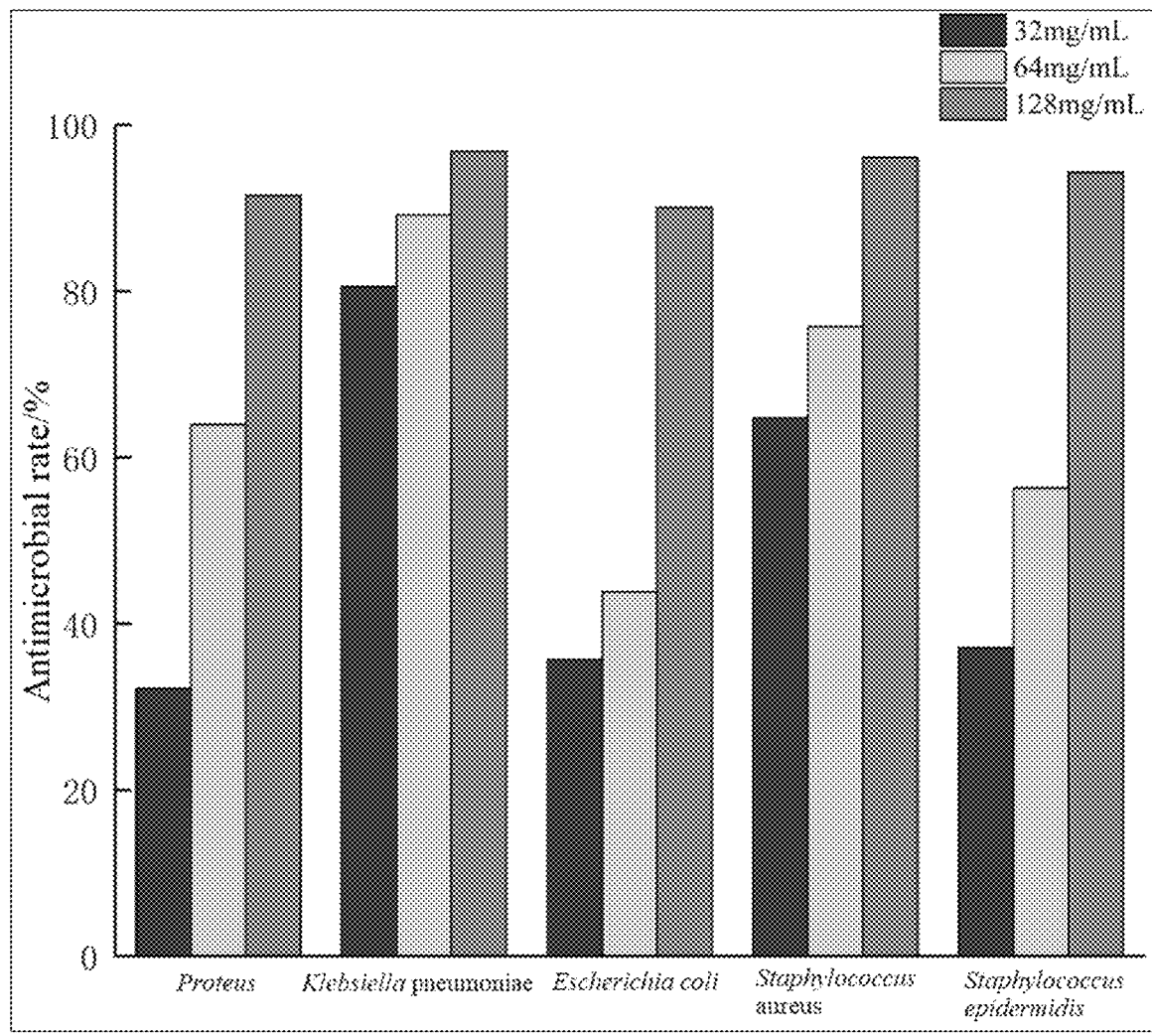
FIG. 2 illustrates antimicrobial rates of bacterial biofilms on surfaces of ureteral stents using the EEP with different concentrations as coatings.
Figure 3:
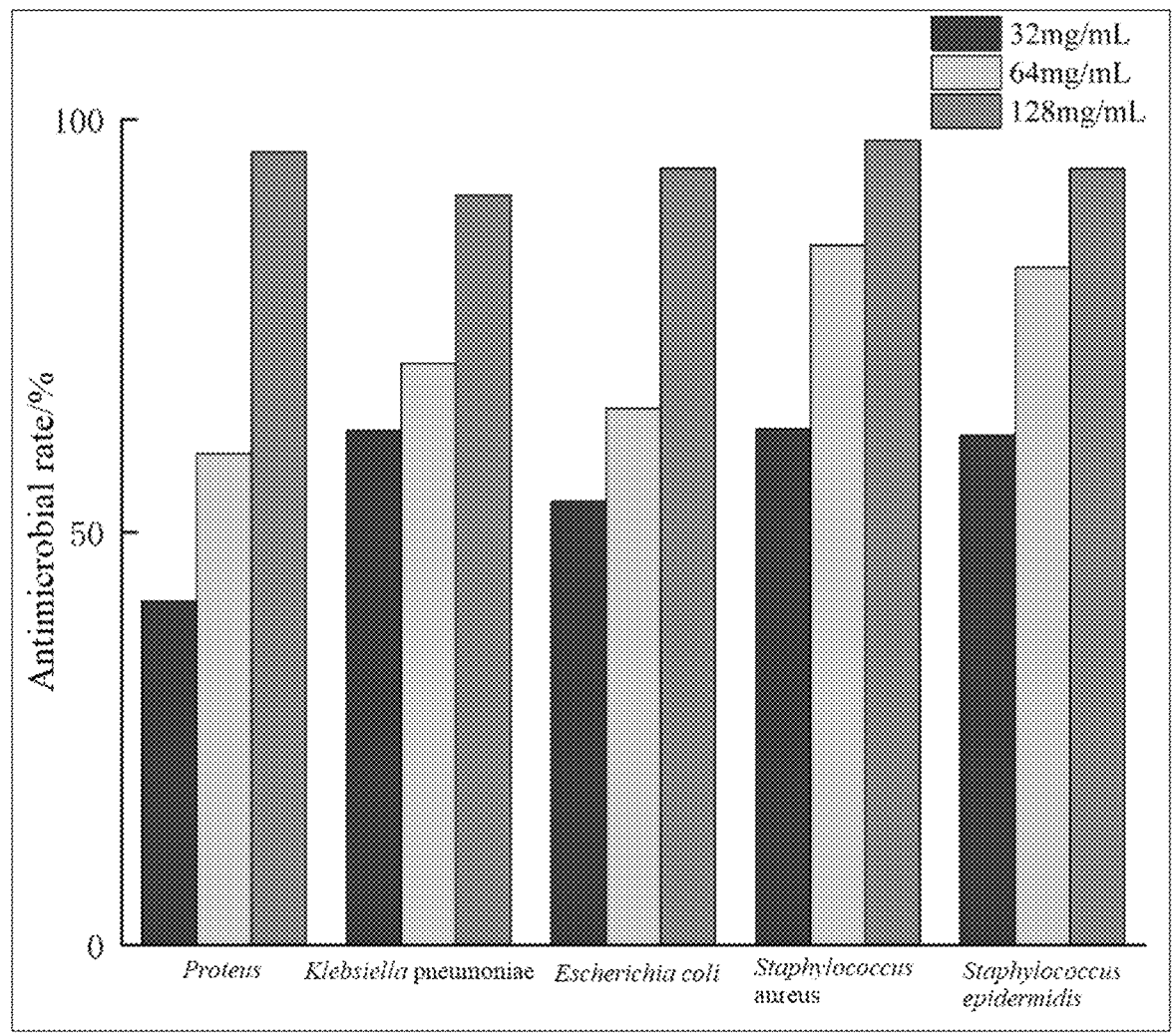
FIG. 3 illustrates antimicrobial rates of bacterial biofilms on the surfaces of the catheters using the EEP with different concentrations as coatings.

(4) Construction of bacterial biofilm includes: placing the aforementioned coatings in 1.5 mL eppendorf (EP) tubes respectively and adding 100 microliters (μL) of 10× diluted bacterial solution with an optical density (OD) of 0.5 and 900 μL mueller hinton (MH) broth in to the EP tubes respectively to incubate at 37° C. for 48 h to construct the bacterial biofilms on the coatings. Afterwards, the segments of the ureteral stent and the catheter are taken out, and then are washed by using phosphate buffer solution (PBS) to remove planktonic bacteria. Then, the segments are placed in EP tubes added with 1 mL of the PBS to perform ultrasonic treatment for 10 min. Thereafter, the EP tubes are diluted according to a gradient, and then are counted according to 100 μL of the diluted solution by using a coating method; and the diluted solution is incubated at 37° C. for 24 h. The antimicrobial rate is calculated by the following formula: (colony counts in the control group−colony counts in the experimental group)/the colony counts in the control group×100%. The experiment repeats three times according to double parallel samples. The antimicrobial rates of the ureteral stents and the catheters using the EEP as coatings are shown in FIG. 2 and FIG. 3, respectively. The control group is composed of the ureteral stents and the catheters using the solvent as coatings, i.e., immersing the ureteral stents and the catheters in the ethanol solution with the volume percentage of 75% for 24 h, then removing and drying in a 37° C. oven. Meanwhile, the experimental group is composed of the ureteral stents and the catheters using the EEP with different concentrations as the coatings (i.e., a low concentration of 32 mg/mL; a medium concentration of 64 mg/mL; and a high concentration of 128 mg/mL).

The results show that the ureteral stents and the catheters using the EEP with three different concentrations as the coatings have a certain inhibitory effect on five common pathogenic bacteria in view of the UTI (i.e., Proteus, Escherichia coli, Klebsiella pneumoniae, Staphylococcus aureus, and Staphylococcus epidermidis). As the concentration of the EEP increases, the antimicrobial rate continues to increase. The antimicrobial rate of the EEP coating with the concentration of 128 mg/mL reaches 80-99%. The results indicate that the EEP coating can effectively inhibit the colonization of common pathogenic bacteria and biofilms on the surface of urinary system catheter, which is beneficial for the prevention and treatment of UTI related to the urinary system catheter.

Experimental Example 2

An antimicrobial property of the catheter prepared by using the EEP as the coating is compared with that of a catheter using a commercially available alloy containing gold, silver, and palladium as a coating.

1. Experimental Method

Figure 4:
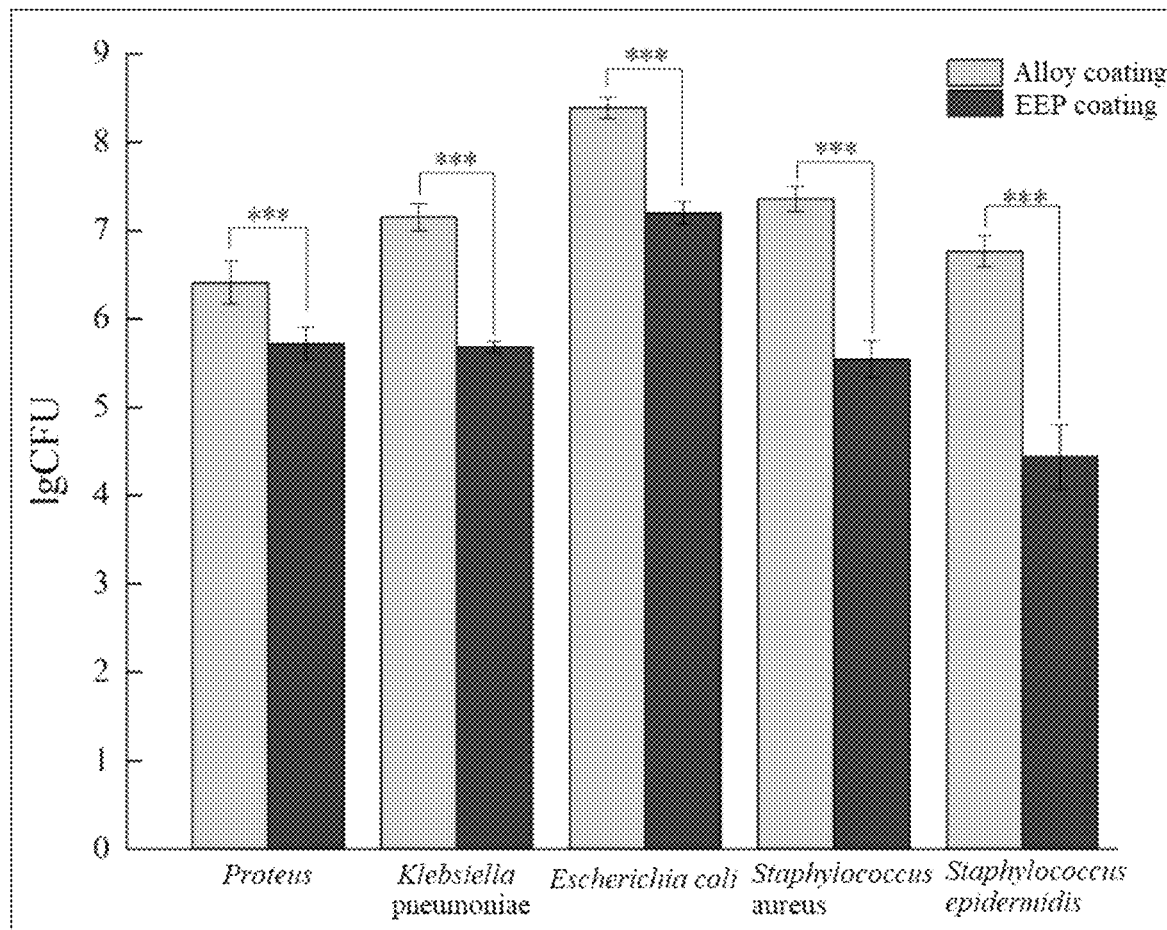
FIG. 4 illustrates a comparison diagram in bacterial counts between a bacterial biofilm on a surface of a catheter using EEP as a coating and a bacterial biofilm on a surface of a catheter using a commercially available alloy containing gold, silver, and palladium as a coating.

The catheter coated with 128 mg/mL of the EEP in a length of 0.5 cm that is prepared by the method as described in the embodiment 1 and the catheter coated with commercially available Bactiguard alloy containing gold, silver, and palladium in a length of 0.5 cm are placed in 1.5 mL EP tubes, respectively, and then 100 μL of 10× diluted bacterial solution with OD of 0.5 and 900 μL MH broth are added into the EP tubes respectively to incubate at 37° C. for 48 h to construct the bacterial biofilms on the coatings. Afterwards, the catheters are taken out, and then are washed by using PBS to remove planktonic bacteria. Then, the catheters are placed in EP tubes added with 1 mL of the PBS to perform ultrasonic treatment for 10 min. Thereafter, the EP tubes are diluted according to a gradient, and then 20 μL of the appropriate diluted solution is taken to calculate the colony counts by using a drip plate method. Specially, each dilution is composed of three parallel samples. After 24 hours of cultivation at 37° C., the colony count is performed and a logarithm relative to the colony count is taken, i.e., LogioCFU (referred to a logarithm of colony-forming unit). The experiment is repeated Three times. The colony counts of the catheters using the EEP and the alloy containing gold, silver, and palladium as the coatings after cultivation are shown in FIG. 4.

2. Experimental Results

The results show that the colony count of the bacterial biofilm on the surface of the catheter using the EEP as the coating is significantly lower than that of the catheter using the commercially available Bactiguard alloy containing the gold, the silver, and the palladium as the coating. The antimicrobial property of the catheter using the EEP as the coating is superior to that of the catheter using the commercially available Bactiguard alloy containing the gold, the silver, and the palladium as the coating. Therefore, the catheter prepared by the present disclosure is beneficial to the inhibition and removal of bacterial biofilm on the surface of the catheter.

Experimental Example 3

A study is provided to research anti-scab property of the ureteral stent prepared by using the EEP as the coating in vivo.

1. Experimental Method (1) Bladder catheterization surgery uses 8 specific pathogen free (SPF) Sprague-Dawley (SD) male rats, each of which is weighed 300 g. After the experimental rats enters the experimental animal house for a week, abdominal cavities of the experimental rats are injected with zoletil according to a dose of 50 milligrams per kilogram (mg/kg) respectively to perform preoperative anesthesia, surgical areas of the experimental rats are shaving and disinfecting, and then the skins and the abdominal muscle layers of the experimental rats are cut at about 2 cm above their pubes to expose their bladders, and small openings are opened on the outer sides of their bladders. Namely, the above group of experimental rats is used as an experimental group. Meanwhile, a control group implants the ureteral stent using a solvent as the coating with a thickness of 0.3 cm into the bladders; and the experimental group implants the ureteral stent using the EEP with the concentration of 128 mg/mL as the coating with a thickness of 0.3 cm into the bladders of the experimental rats. Thereafter, the bladders are sutured by using purse-string suture, and then the experimental group and the control group are injected with 0.1 mL of Proteus fluid according to a concentration of 106 colony-forming unit per milliliter (CFU/mL) by using an insulin needle to feed into the bladders of the rats in the experimental group and the control group; and the muscle layers and skins are subjected to the suturing, disinfection of wounds, and postoperative observation respectively. The ureteral stent using the solvent as the coating in the control group is prepared by immersing the ureteral stent with the thickness of 0.3 cm in the ethanol solution with the volume percentage of 75% according to the method used in the control group of the experimental example 1. The ureteral stent using the EEP as the coating in the experimental group is prepared by immersing the ureteral stent with the thickness of 0.3 cm in the EEP with the concentration of 128 mg/mL according to the method used in the experimental group of the experimental example 1.

(2) Collection and measurement of scabs includes: after implanting the coated ureteral stents in the rats of the experimental group and the control group for a month, injecting the abdominal cavities of the rats with the zoletil according to a dose of 100 mg/kg to kill the rats. Then, the ureteral stents inside the bladders are taken out by dissection; surface crystals of the ureteral stents are removed by deionized water, and weighed after drying at room temperature. Thereafter, stones on the ureteral stents of the experimental group and the control group are carefully scraped to place into 150 ml conical flasks respectively, and then the conical flasks are added with 5 mL of mixed acid solution (i.e., according to nitric acid: perchloric acid being 9:1) respectively; and the conical flasks are heated and dissolved on an electric heating plate from a low temperature (80° C.) to a high temperature (180° C.). Furthermore, if the conical flask appears brownish black, the mixed acid solution is added again until the conical flask emits white smoke and the solution in the conical flask appears clear or light yellow transparent state. Thereafter, the conical flasks are subjected to the high temperature to remove the acid until a volume of the solution therein is 0.5 mL. Then, the samples (i.e., the stones in the conical flasks) are removed from the electric heating plate and cooled down to the room temperature, after cooling, the solution is washed with a small amount of deionized water for multiple times, and then to move to a 100 mL volumetric flask, and the solution is fixed to a scale line with a mass percentage of 1% lanthanum oxide solution and shaken up to obtain a to-be-detected sample digestion solution. A blank group is not added with the sample, and the rest is the same as the above operations to obtain a blank digestion solution. Then, calcium and magnesium contents in each group of digestive solution are measured by using a flame atomic absorption spectrometer, and are quantified according to standard curve is quorum.

2. Experimental Results

Figure 5:
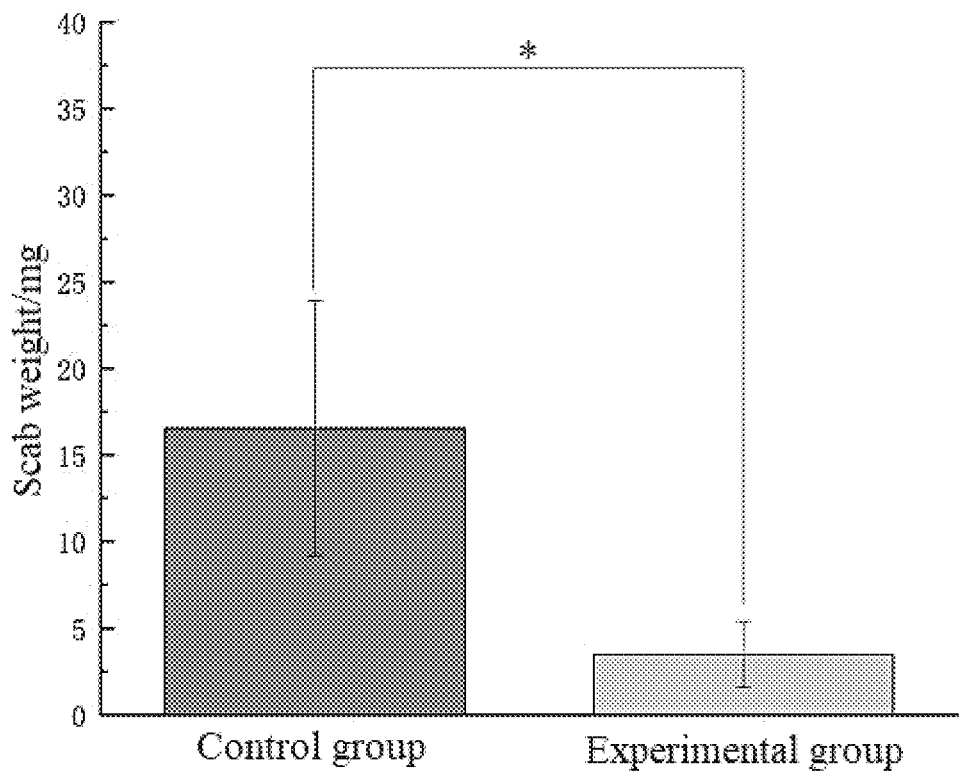
FIG. 5 illustrates a schematic diagram of measurement results of scab weights generated on the surfaces of each group of ureteral stents.
Figure 6:
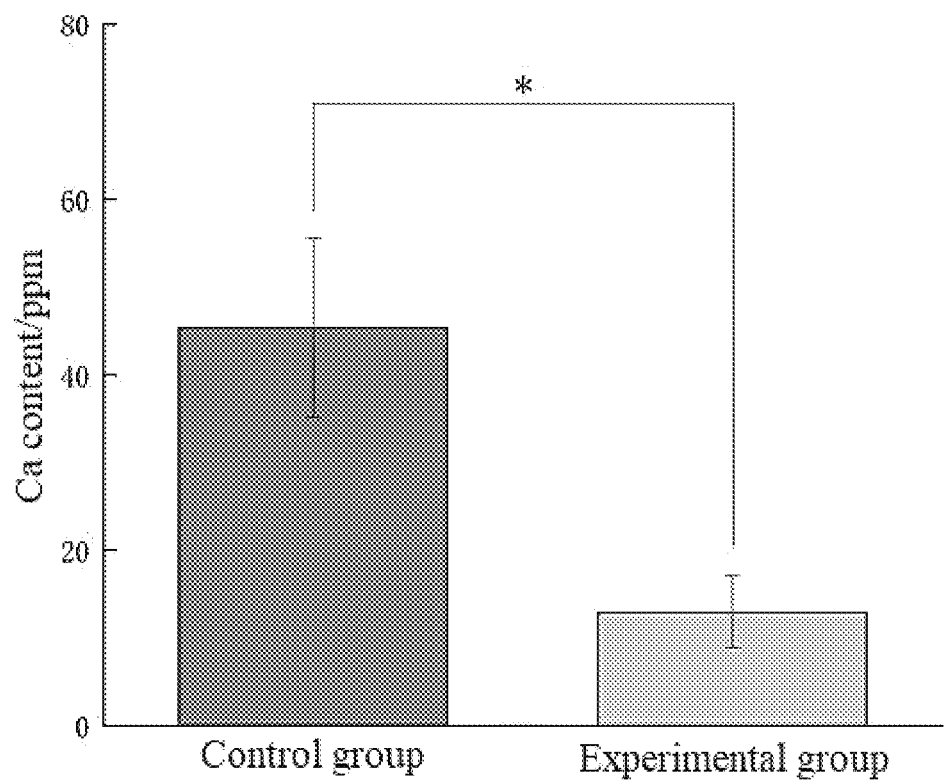
FIG. 6 illustrates a schematic diagram of measurement results of calcium contents on the surfaces of each group of ureteral stents.

The measurement results of scab weights on the surfaces of the ureteral stents in the control group and the experimental group, as well as the calcium and magnesium contents on the surfaces of the ureteral stents are shown in Table 3 and FIGS. 5-6.

TABLE 3

Measurement results (average value) of the scab weights and the calcium and magnesium contents on the surfaces of the ureteral stents in the control group and the experimental group

| Group | Scab weight/mg | Calcium content | Magnesium content |
|---|---|---|---|
| Control group | 16.540 | 45.330 | 0.774 |
| Experimental group | 3.500 | 12.950 | 0 |

The results show that the scab weight on the surface and the calcium and magnesium contents in the scab of the ureteral stent using the EEP as the coating are significantly lower than those of the ureteral stent using the solvent as the coating, and the results all have statistical significance. Namely, the EEP coating helps to prevent the stones and scabs forming on the surface of the ureteral stent.

In summary, the propolis alcohol extract according to the present disclosure is used as the coating covered on the urinary system catheter to prepare the antimicrobial and anti-infective urinary system catheter. As the surface coating, the propolis alcohol extract can enhance the hydrophilicity of the surface of the urinary system catheter, avoid the problem of discomfort of the patient caused by the friction during the clinical operation, and facilitate the clinical operation of the urinary system catheter. Meanwhile, the propolis alcohol extract as the surface coating prevents the surface of the urinary system catheter from forming a bacterial biofilm, has excellent antimicrobial and anti-infective properties, and performs well in anti-encrustation. In addition, the propolis is a natural substance, which has the advantages of good biocompatibility and low cost, and is suitable for mass production. The urinary system catheter prepared by using the propolis alcohol extract as the coating can effectively solve the problems of the urinary system catheter in the related art (i.e., the clinical operation is inconvenient, the bacterial biofilm is formed, the scab is generated, the biocompatibility is poor, the cost is high, the mass production is difficult, etc.), and has a good application prospect. Moreover, flavonoids and phenolic acids generated by the propolis and the propolis alcohol extract endow the urinary system catheter antimicrobial and anti-calculi properties.

Obviously, according to the above content of the present disclosure, other various forms of modifications, substitutions or alterations can be made without departing from the basic technical idea of the present disclosure according to common technical knowledge and customary means in the related art.

The present disclosure is further described in detail with reference to the illustrated embodiments described above. However, it should not be understood that the scope of the present disclosure described above is limited to the embodiments only. All techniques implemented based on the foregoing content of the present disclosure fall within the scope of the present disclosure.

What is claimed is:

1. An antimicrobial and anti-infective urinary system catheter, comprising:
    a surface of a urinary system catheter; and
    a coating of a propolis alcohol extract directly covered on the surface of the urinary system catheter, to enhance hydrophilicity of the surface of the urinary system catheter, prevent stones and scabs forming on the surface of the urinary system catheter, and make the urinary system catheter antimicrobial and anti-infective;
    wherein the propolis alcohol extract is an ethanol extract of propolis, and a preparation method of the ethanol extract of propolis comprises the following steps: adding ethanol into propolis to perform ultrasonic extraction to obtain an extract, and filtering the extract to obtain supernatant, thereby obtaining the ethanol extract of propolis;
    wherein the ethanol is an ethanol solution with a volume percentage of 75%;
    wherein a mass of the ethanol is 25 times of a mass of the propolis;
    wherein a temperature of the ultrasonic extraction is 60 degrees Celsius (° C.), a frequency of the ultrasonic extraction is 37 kilohertz (kHz), a power of the ultrasonic extraction is 100 watts (W), and a time for the ultrasonic extraction is 60 minutes (min); and
    wherein a method for covering the surface of the urinary system catheter with the coating of the propolis alcohol extract comprises the following steps: immersing the urinary system catheter into a solution of the ethanol extract of propolis, and then taking out and drying to obtain the antimicrobial and anti-infective urinary system catheter;
    wherein a solvent of the solution of the ethanol extract of propolis is the ethanol with the volume percentage of 75%, and a concentration of the solution of the ethanol extract of propolis is in a range of 32 milligrams per milliliter (mg/mL) to 128 mg/mL;
    wherein the coating of the propolis alcohol extract comprises: total flavonoids and total phenolic acid, and an average surface propolis content of the coating of the propolis alcohol extract is greater than or equal to 0.721 according to the following formula for calculating the average surface propolis content:

$$\frac{\text{total flavonoids content in solution}/274.4 + \text{total phenolic acid content in solution}/143.7}{2 \times \text{surface area of segment}}$$

where total flavonoids content in solution represents content of the total flavonoids in a dissolved solution of the coating of the propolis alcohol extract, total phenolic acid content in solution represents content of the total phenolic acid in the dissolved solution of the coating of the propolis alcohol extract, surface area of segment represents an area of the surface of the urinary system catheter coated with the coating of the propolis alcohol extract; and
    wherein a contact angle between the coating of the propolis alcohol extract covered on the surface of the urinary system catheter and water is less than 90°.

2. The antimicrobial and anti-infective urinary system catheter as claimed in claim 1, wherein the urinary system catheter is a ureteral stent, a catheter, a urethral stent, a prostate stent, a cystostomy catheter, a nephrostomy catheter, or a urological guidewire.

3. The antimicrobial and anti-infective urinary system catheter as claimed in claim 1, wherein the contact angle between the coating of the propolis alcohol extract covered on the surface of the urinary system catheter and the water is less than 60°.

4. The antimicrobial and anti-infective urinary system catheter as claimed in claim 1, wherein the total flavonoids is 274.4±4.4 mg/g, and the total phenolic acid is 143.7±0.3 mg/g.

5. The antimicrobial and anti-infective urinary system catheter as claimed in claim 1, wherein the urinary system catheter is a ureteral stent, a concentration of the propolis alcohol extract is 32 mg/mL, and the average surface propolis content is 0.721 mg/cm$^2$.

6. The antimicrobial and anti-infective urinary system catheter as claimed in claim 1, wherein the urinary system catheter is a ureteral stent, a concentration of the propolis alcohol extract is 64 mg/mL, and the average surface propolis content is 1.598 mg/cm$^2$.

7. The antimicrobial and anti-infective urinary system catheter as claimed in claim 1, wherein the urinary system catheter is a ureteral stent, a concentration of the propolis alcohol extract is 128 mg/mL, and the average surface propolis content is 4.072 mg/cm$^2$.

8. The antimicrobial and anti-infective urinary system catheter as claimed in claim 1, wherein the urinary system catheter is a catheter, a concentration of the propolis alcohol extract is 32 mg/mL, and the average surface propolis content is 1.163 mg/cm$^2$.

9. The antimicrobial and anti-infective urinary system catheter as claimed in claim 1, wherein the urinary system catheter is a catheter, a concentration of the propolis alcohol extract is 64 mg/mL, and the average surface propolis content is 4.134 mg/cm$^2$.

10. The antimicrobial and anti-infective urinary system catheter as claimed in claim 1, wherein the urinary system catheter is a catheter, a concentration of the propolis alcohol extract is 128 mg/mL, and the average surface propolis content is 6.451 mg/cm$^2$.

* * * * *